United States Patent
Gerber et al.

(10) Patent No.: US 7,501,045 B2
(45) Date of Patent: Mar. 10, 2009

(54) METHOD OF PRODUCING AND SEPARATING DINITRILE COMPOUNDS

(75) Inventors: Jérôme Gerber, Lyons (FR); Philippe Leconte, Meyzieu (FR); Daniel Amoros, Venissieux (FR)

(73) Assignee: Rhodia Polyamide Intermediates, Saint-Fons (FR)

( * ) Notice: Subject to any disclaimer, the term of this patent is extended or adjusted under 35 U.S.C. 154(b) by 391 days.

(21) Appl. No.: 10/565,483

(22) PCT Filed: Jul. 23, 2004

(86) PCT No.: PCT/FR2004/001972
§ 371 (c)(1),
(2), (4) Date: Jan. 20, 2006

(87) PCT Pub. No.: WO2005/019160
PCT Pub. Date: Mar. 3, 2005

(65) Prior Publication Data
US 2006/0175189 A1  Aug. 10, 2006

(30) Foreign Application Priority Data
Jul. 25, 2003 (FR) .................. 03 09152

(51) Int. Cl.
*B01D 3/14* (2006.01)
*B01D 3/42* (2006.01)
*C07C 253/34* (2006.01)
*C07C 253/10* (2006.01)

(52) U.S. Cl. ............... 203/1; 203/98; 203/99; 203/DIG. 19; 558/456; 558/465

(58) Field of Classification Search ............ 203/1, 203/2, 98, 99, DIG. 19; 558/456, 463, 465
See application file for complete search history.

(56) References Cited

U.S. PATENT DOCUMENTS

| | | | | | |
|---|---|---|---|---|---|
| 4,230,634 | A | * | 10/1980 | Benzie et al. | 558/339 |
| 4,599,145 | A | * | 7/1986 | Kawakami et al. | 203/71 |
| 6,139,693 | A | * | 10/2000 | Bassler et al. | 203/49 |
| 6,599,398 | B1 | * | 7/2003 | Ostermaier et al. | 203/74 |
| 6,852,199 | B2 | * | 2/2005 | Jungkamp et al. | 203/91 |
| 6,860,971 | B2 | * | 3/2005 | Ward et al. | 203/14 |
| 2007/0287851 | A1 | * | 12/2007 | Scheidel et al. | 558/355 |

FOREIGN PATENT DOCUMENTS

DE  12 68 611 B  5/1968

OTHER PUBLICATIONS

International Search Report for PCT/FR2004/001972, Jan. 18, 2005, B. Zervas.

* cited by examiner

*Primary Examiner*—Virginia Manoharan
(74) *Attorney, Agent, or Firm*—Buchanan, Ingersoll & Rooney P.C.

(57) ABSTRACT

The present invention relates to a process for the manufacture and separation of dinitrile compounds.

It relates more particularly to a process for the manufacture and separation of dinitrile compounds from a medium originating from the hydrocyanation of unsaturated mononitriles.

The invention consists in feeding the medium comprising the dinitriles to a distillation column and then recovering the purified dinitriles as intermediate fraction, the heavy products being removed as column tail fraction and the light products, including the unsaturated mononitriles, being recovered as top fraction.

8 Claims, 1 Drawing Sheet

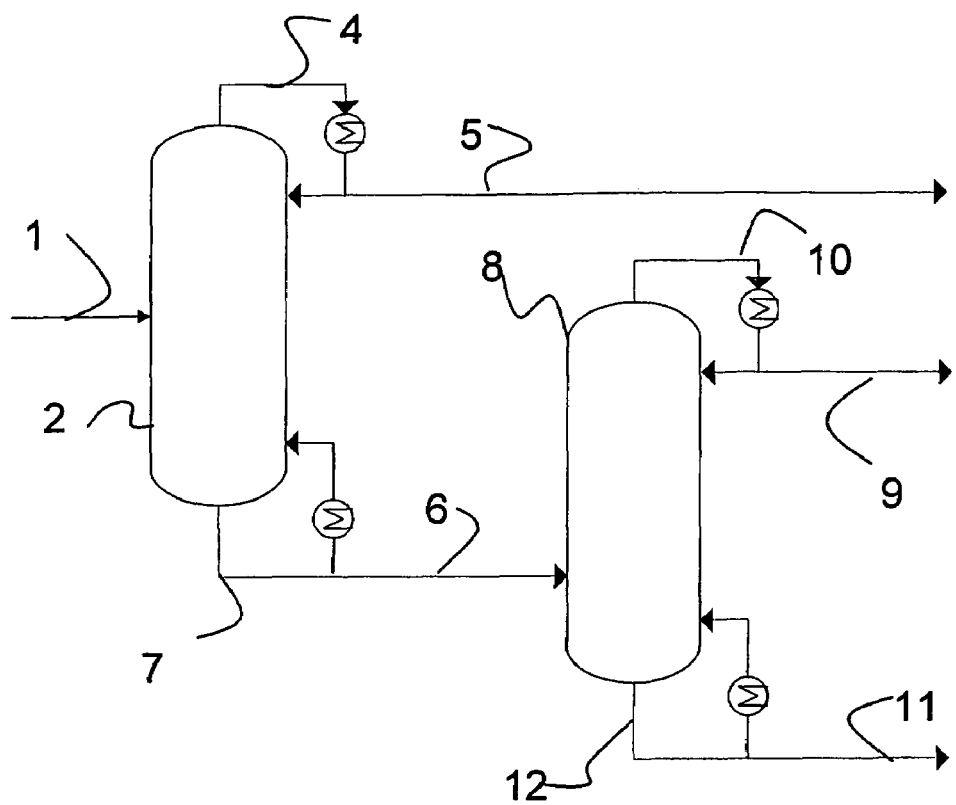
Fig. 1 - Prior Art
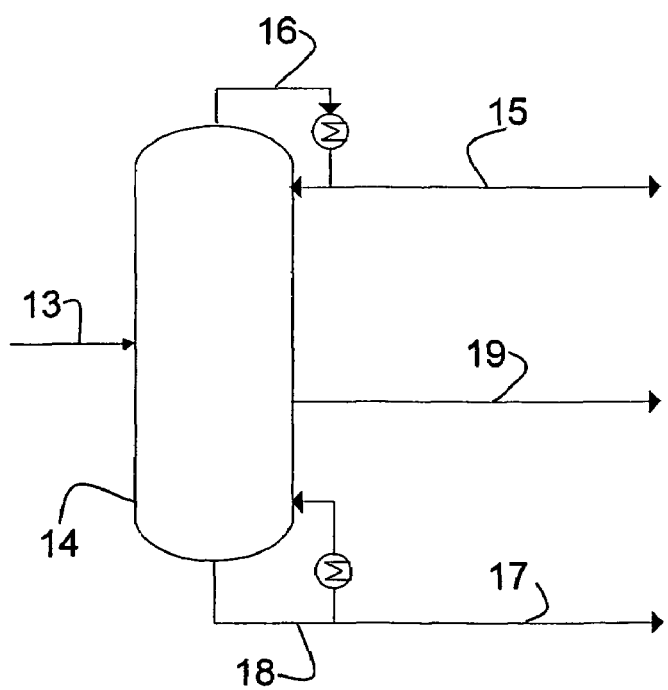
Fig. 2

METHOD OF PRODUCING AND SEPARATING DINITRILE COMPOUNDS

This application is an application under 35 U.S.C. Section 371 of International Application Number PCT/FR2004/001972, filed on Jul. 23, 2004.

The present invention relates to a process for the manufacture and separation of dinitrile compounds.

It relates more particularly to a process for the manufacture and separation of dinitrile compounds from a medium originating from the hydrocyanation of unsaturated mononitriles.

Dinitrile compounds, such as adiponitrile, are important chemical intermediates in the manufacture of numerous compounds. Adiponitrile is in particular a chemical intermediate in the synthesis of various monomers used in the manufacture of polymers, such as polyamides.

Furthermore, the process for the synthesis of dinitrile compounds used industrially consists in carrying out a two-stage hydrocyanation of diolefins, for example of butadiene.

In a first stage, the synthesis makes it possible to produce unsaturated mononitriles. The latter are used as starting material in a second stage in order to be converted to dinitriles by reaction with a molecule of hydrogen cyanide. Generally, these two stages are carried out successively with movement of the various streams, such as, for example, the stream of the catalytic system, between these stages. However, they can be carried out separately and independently.

The reaction medium resulting from the second stage comprises the dinitriles formed, the unconverted mononitriles and the catalytic system, as well as various by-products.

The processes comprise stages for the treatment of this reaction medium in order, on the one hand, to separate the catalytic system and, on the other hand, to separate the dinitriles from the mononitriles, which will advantageously be recycled.

The separation of the catalytic system is generally obtained by separation by settling and/or by liquid/liquid extraction with an extraction solvent, such as hydrocarbons.

The organic phase comprising the mononitriles and dinitriles is treated in a distillation stage in order to separate the mononitriles from the dinitriles, on the one hand, and the heavy products, on the other hand. This distillation stage comprises, in current processes, two distillation columns; in a first column, the products with a lower boiling point than that of the dinitriles, such as the mononitriles, are separated and recovered at the column top; the heavy fraction comprising the dinitriles is fed to a second distillation column, making it possible to distil the dinitriles, which are recovered at the column top.

There are several disadvantages to this process, including that of maintaining the dinitrile compounds at a high temperature for a relatively long period of time.

Maintaining the dinitrile compounds at a high temperature promotes the formation of by-products originating from the decomposition of the dinitriles. Thus, in the case of adiponitrile, one by-product, iminocyanocyclopentane (TCCP), is formed in particular. This by-product is very difficult to separate from adiponitrile. In addition, in processes for the conversion of adiponitrile to other compounds, such as, for example, to hexamethylenediamine, the by-products can be converted to other compounds which are difficult to separate. Thus, during the hydrogenation of adiponitrile to hexamethylenediamine, the ICCP is converted to aminomethylenecyclopentaneamine (AMCPA). These impurities cannot be accepted in processes for the manufacture of polymers, such as polyamide, in particular when the latter are used for the manufacture of textile yarns.

One of the aims of the present invention is to overcome these disadvantages by providing a novel process for the preparation and separation of dinitrile compounds which makes it possible, in particular, to limit and minimize the formation of by-products during the recovery and extraction of the dinitrile compounds formed.

A subject-matter of the present invention is a process for the manufacture and separation of dinitriles from a medium originating from the hydrocyanation of unsaturated mononitriles, characterized in that it consists in feeding the medium comprising the dinitriles to a distillation column at the level of a theoretical plate of the column recovering, at the column top, the compounds with a lower boiling point than that of the dinitriles recovering the intermediate fraction comprising the dinitriles from a theoretical plate situated in a lower part of the column with respect to the plate for feeding the medium comprising the dinitriles recovering the products with a higher boiling point than that of the dinitriles at the column bottom.

BRIEF DESCRIPTION OF THE DRAWINGS

FIG. 1 represents a block diagram of a plant for the separation of dinitriles of the prior art.

FIG. 2 represents a diagram of an embodiment of a plant for the separation of dinitriles in accordance with the invention.

According to one characteristic of the invention, the column bottom temperature is less than 200° C., preferably between 140° C. and 190° C. Such a column bottom temperature makes it possible to limit the formation of by-products, in particular by thermal decomposition of the dinitriles. The term "column bottom temperature" is understood to mean the temperature of the liquid phase in the boiler of the column and the wall temperature of the said boiler.

Advantageously, the intermediate fraction comprising the dinitriles is recovered without reflux or with a reflux. The reflux ratio can represent from 1 to 6% by weight of the fraction recovered. The reflux can be introduced into the column at the same level as the withdrawal of the said fraction or at a different level.

According to another characteristic of the invention, the dinitrile compounds produced by the process of the invention are compounds of following general formula (I):

$$NC\text{---}R\text{---}CN \qquad (I)$$

in which the R radical represents a saturated hydrocarbonaceous radical comprising from 2 to 10 carbon atoms.

The preferred dinitrile compounds of the invention are chosen from the group consisting of adiponitrile, methylglutaronitrile and ethylsuccinonitrile.

The distillation is carried out under an appropriate pressure according to the nature of the dinitrile compounds to be separated, preferably at a pressure of between 1 kPa and 5 kPa.

The distillation of the invention can be carried out in any suitable device, such as a plate column, a packed column or a partition column. The number of theoretical plates of the column is determined according to the nature of the compounds to be treated. Generally, columns exhibiting a number of theoretical plates of between 6 and 20 are suitable for the invention.

The intermediate fraction comprising the dinitrile compounds is withdrawn from the distillation column advantageously in the liquid state or in the vapour state. The fraction collected at the column top comprises, in the case of a hydrocyanation process, the unsaturated mononitriles present in the medium.

The process of the invention makes it possible to recover dinitriles comprising a very low amount of by-products originating from the thermal decomposition of the dinitrile compounds. The dinitriles thus recovered can be subjected to a separation, for example by distillation, to recover, on the one hand, adiponitrile, and, on the other hand, the other dinitriles formed, such as methylglutaronitrile or ethylsuccinonitrile.

Furthermore, the process of the invention makes it possible to obtain dinitrile compounds comprising a very low concentration of impurities while using a single distillation column, that is to say with reduced capital and operating costs in comparison with current plants comprising two columns arranged in series.

Other advantages and details of the invention will become more clearly apparent in the light of the description of an implementational example of the process of the invention, given solely by way of illustration and made with reference to the appended figures, for which a brief description is given hereinabove.

COMPARATIVE EXAMPLE 1

With reference to FIG. 1, a mixture resulting from a process for the manufacture of adiponitrile by hydrocyanation of pentenenitriles in the presence of a catalytic system comprising an organometallic complex of nickel and of tritolyl phosphite and of a Lewis acid ($ZnCl_2$) is fed at 1 to a first distillation column 2 comprising a packing and exhibiting a number of theoretical plates of 6. The column bottom temperature is 161° C. and the operating pressure is 2 kPa.

A top fraction 5 is withdrawn with a reflux 4. The withdrawn fraction 5 comprises the products exhibiting a boiling point below that of adiponitrile or more generally below those of the dinitriles present in the medium. As is indicated in Table I below, this top fraction is composed mainly of pentenenitriles which have not been converted to dinitriles.

The liquid present at the column bottom circulates in a loop 7 comprising a boiler. A tail fraction 6 is withdrawn at the bottom of column 2 or from this circulation.

This fraction 6 is fed to a second distillation column 8. In the example illustrated, the column 8 is similar to the column 2. The column bottom temperature is 164° C. and the pressure is 2 kPa.

Fraction 6 is fed at the level of an intermediate plate of the column 8. The dinitriles, including adiponitrile, are recovered in the form of a top fraction 9, with a reflux 10.

The compounds with a higher boiling point than that of adiponitrile and of the dinitriles present are recovered in the form of a tail fraction 11. As in the column 2, the liquid present in the column bottom is circulated 12 with the presence of a boiler in the circulation loop.

The compositions of the various fractions are shown in Table I below.

The residence time of the mixture and in particular of the adiponitrile and the dinitriles is the sum of the residence times in the columns 2 and 8.

The ICCP concentration in the top fraction 9 of the second column 8 is 0.08% by weight.

TABLE I

|  | Mixture 1 | Fraction 5 | Fraction 6 | Fraction 9 | Fraction 11 |
|---|---|---|---|---|---|
| Pentenenitriles (% by weight) | 19.6 | 97.6 | 0.16 | 0.17 | 0 |
| Dinitriles (% by weight) | 80 | 2.4 | 99.34 | 99.82 | 90.99 |
| Heavy compounds (% by weight) | 0.4 | 0 | 0.5 | 0.01 | 9.01 |
| Total stream (kmol/h) | 1 | 0.2 | 0.8 | 0.76 | 0.04 |

The term "heavy compounds" denotes the compounds with a higher boiling point than that of adiponitrile

EXAMPLE 2

With reference to FIG. 2, a mixture corresponding to that of Example 1 is fed at 13 to an intermediate plate of a packed distillation column 14. This column exhibits 6 theoretical plates and operates under a pressure of 2 kPa with a column bottom temperature of 164° C.

The compounds with a lower boiling point than those of the dinitriles present, more particularly than that of adiponitrile, are recovered in the form of a top fraction 15 with a reflux 16. The composition of this top fraction 15 is shown in Table II below and comprises in particular the unconverted pentenenitriles.

The compounds with a higher boiling point than those of the dinitriles present, more particularly than that of adiponitrile, are recovered at the bottom of column 14 in the form of a bottom fraction 17 with circulation of the liquid at the column bottom through a loop 18 comprising a boiler. The bottom fraction 17 can advantageously be concentrated before being recycled in the loop 18.

The dinitriles, including adiponitrile, are recovered in an intermediate fraction 19 by withdrawing from an intermediate plate situated at a lower position with respect to that at which the mixture to be treated is fed 13.

The compositions of the various fractions are shown in Table II below.

The residence time of the mixture and in particular of the dinitriles, including adiponitrile, is of the same order of magnitude as that observed in the column 8 of Example 1. Thus, the process of the invention makes it possible to separate and recovery the dinitriles, including adiponitrile, with a residence time of this compound in the distillation column which is lower than that observed in Example 1. This is because the residence time in the column 2 is eliminated with the process of the invention.

The process of the invention makes it possible to recover dinitriles comprising 0.04% by weight of ICCP.

TABLE II

|  | Mixture 1 | Fraction 15 | Fraction 19 | Fraction 17 |
|---|---|---|---|---|
| Pentenenitriles (% by weight) | 19.6 | 97.6 | 0.17 | 0 |
| Adiponitrile (% by weight) | 80 | 2.4 | 99.82 | 90.99 |

TABLE II-continued

|  | Mixture 1 | Fraction 15 | Fraction 19 | Fraction 17 |
|---|---|---|---|---|
| Heavy compounds (% by weight) | 0.4 | 0 | 0.01 | 9.01 |
| Total stream (kmol/h) | 1 | 0.2 | 0.76 | 0.04 |

The invention claimed is:

1. A process for the manufacture and separation of dinitriles from a medium originating from a hydrocyanation of unsaturated mononitriles, comprising the steps of:
   a) feeding the medium comprising the dinitriles to a distillation column,
   b) recovering, at the column top, compounds with a lower boiling point than that of the dinitriles,
   c) recovering an intermediate fraction comprising the dinitriles from a theoretical plate situated in a lower part of the column with respect to a feed point of the medium comprising the dinitriles, and
   d) recovering, at the column bottom, products with a higher boiling point than that of the dinitriles,
   wherein the recovery of the intermediate fraction is carried out either without reflux or with reflux with a reflux ratio of between 1 and 6% by weight of the intermediate fraction.

2. The process according to claim 1, wherein the column bottom is at a temperature of less than 200° C., optionally between 140° C. and 190° C.

3. The process according to claim 1, wherein the dinitrile compounds are compounds of following general formula (I):

NC—R—CN　(I)

in which the R radical represents a saturated hydrocarbonaceous radical having from 2 to 10 carbon atoms.

4. The process according to claim 3, wherein the dinitriles are adiponitrile, methylglutaronitrile or ethylsuccinonitrile.

5. The process according to claim 1, wherein said process is carried out under a pressure of between 1 kPa and 5 kPa.

6. The process according to claim 1, wherein the distillation column is a plate column, a packed column or a partition column.

7. A process for the manufacture and separation of dinitriles from a medium originating from a hydrocyanation of unsaturated mononitriles, comprising the steps of:
   a) feeding the medium comprising the dinitriles to a distillation column,
   b) recovering, at the column top, compounds with a lower boiling point than that of the dinitriles,
   c) recovering an intermediate fraction comprising the dinitriles from a theoretical plate situated in a lower part of the column with respect to a feed point of the medium comprising the dinitriles, and
   d) recovering, at the column bottom, products with a higher boiling point than that of the dinitriles,
   wherein the recovery of the intermediate fraction is carried out without reflux.

8. A process for the manufacture and separation of dinitriles from a medium originating from a hydrocyanation of unsaturated mononitriles, comprising the steps of:
   a) feeding the medium comprising the dinitriles to a distillation column,
   b) recovering, at the column top, compounds with a lower boiling point than that of the dinitriles,
   c) recovering an intermediate fraction comprising the dinitriles from a theoretical plate situated in a lower part of the column with respect to a feed point of the medium comprising the dinitriles, and
   d) recovering, at the column bottom, products with a higher boiling point than that of the dinitriles,
   wherein the recovery of the intermediate fraction is carried out with a reflux ratio of between 1 and 6% by weight of the intermediate fraction.

* * * * *